United States Patent
Ashwood et al.

[11] Patent Number: 6,046,325
[45] Date of Patent: Apr. 4, 2000

[54] CHEMICAL SYNTHESIS OF 1,4-OXAZIN-2-ONES

[75] Inventors: Michael Stewart Ashwood; Brian Christopher Bishop, both of Bishops Stortford; Ian Frank Cottrell, Hertford, all of United Kingdom

[73] Assignee: Merck Sharp & Dohme Limited, Hoddesdon, United Kingdom

[21] Appl. No.: 09/391,705

[22] Filed: Sep. 8, 1999

[30] Foreign Application Priority Data

Sep. 11, 1998 [GB] United Kingdom .................. 9819890

[51] Int. Cl.[7] ................................................. C07D 265/32
[52] U.S. Cl. ............................................................. 544/173
[58] Field of Search ............................................... 544/173

[56] References Cited

U.S. PATENT DOCUMENTS 5,668,280 9/1997 Alabaster et al. ...................... 544/173
5,719,147 2/1998 Dorn et al. ............................ 514/227.5

OTHER PUBLICATIONS

Agami, et al., *Tetrahedron Lett.*, 34, 7061 (1993).
Evans, et al., *J. Am. Chem. Soc.*, 112, 4011–4030 (1990).

*Primary Examiner*—Joseph McKane
*Attorney, Agent, or Firm*—J. Eric Thies; David L. Rose

[57] ABSTRACT

The present invention relates to a process for the preparation of a compound of formula (I):

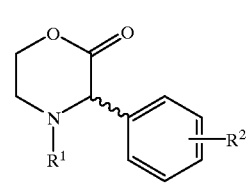

(I)

wherein $R^1$ is a $C_{1-6}$alkyl or aryl$C_{1-4}$alkyl group; and $R^2$ is a hydrogen atom, a halogen atom, or a group selected from $C_{1-6}$alkyl, $CF_3$ or $C_{1-6}$alkoxy substituted by $C_{1-4}$alkoxy; which comprises reacting an anhydrous or hydrated glyoxal of formula (II) with a compound of formula (III):

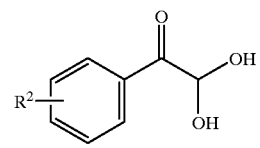

(II)

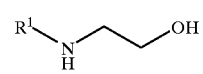

(III)

in the presence of an acid.

10 Claims, No Drawings

CHEMICAL SYNTHESIS OF 1,4-OXAZIN-2-ONES

The present invention relates to a process for the preparation of 1,4-oxazin-2-one derivatives which are useful as intermediates in the preparation of certain therapeutic agents. In particular, the present invention provides a process for the preparation of N-benzyl-3-(4-fluorophenyl)-1,4-oxazin-2-one and N-((S)-(−)-α-methylbenzyl)-3-(4-fluorophenyl)-1,4-oxazin-2-one which are intermediates in the preparation of pharmaceutical compounds which are substance P (or neurokinin-1) receptor antagonists.

European patent specification No. 0 577 394-A (published 5th January 1994) describes the preparation of 3-(S)-(4-fluorophenyl)-4-benzyl-2-morpholinone (hereinafter referred to as N-benzyl-3-(S)-(4-fluorophenyl)-1,4-oxazin-2-one), which has the structure:

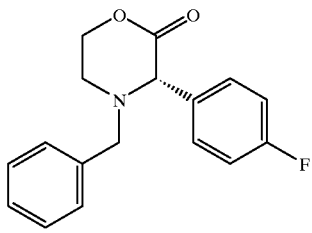

by a two-step process starting from optically pure (S)-(4-fluorophenyl) glycine. Control of process parameters (e.g. reaction time, temperature, moisture content) is necessary to prevent racemisation in these steps. With reference to Example 59 in EP-0 577 394-A, the 1,4-oxazin-2-one is prepared as follows:

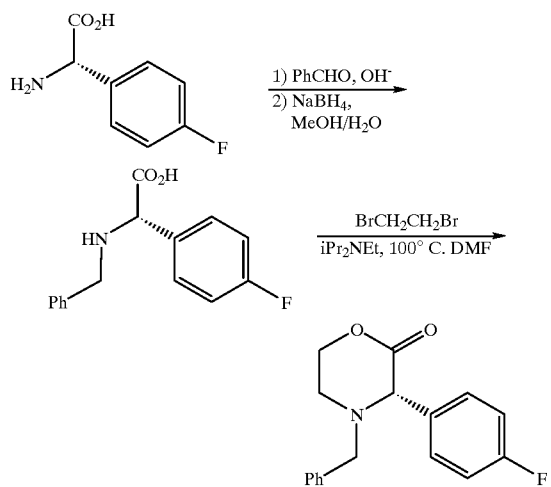

Furthermore, the preparation of optically pure (S)-(4-fluorophenyl)glycine is described in EP-0 577 394-A by means of a four-step asymmetric synthesis process which is not amenable to reproduction on a production scale. In particular, Example 58 in EP-0 577 394-A describes the following synthesis:

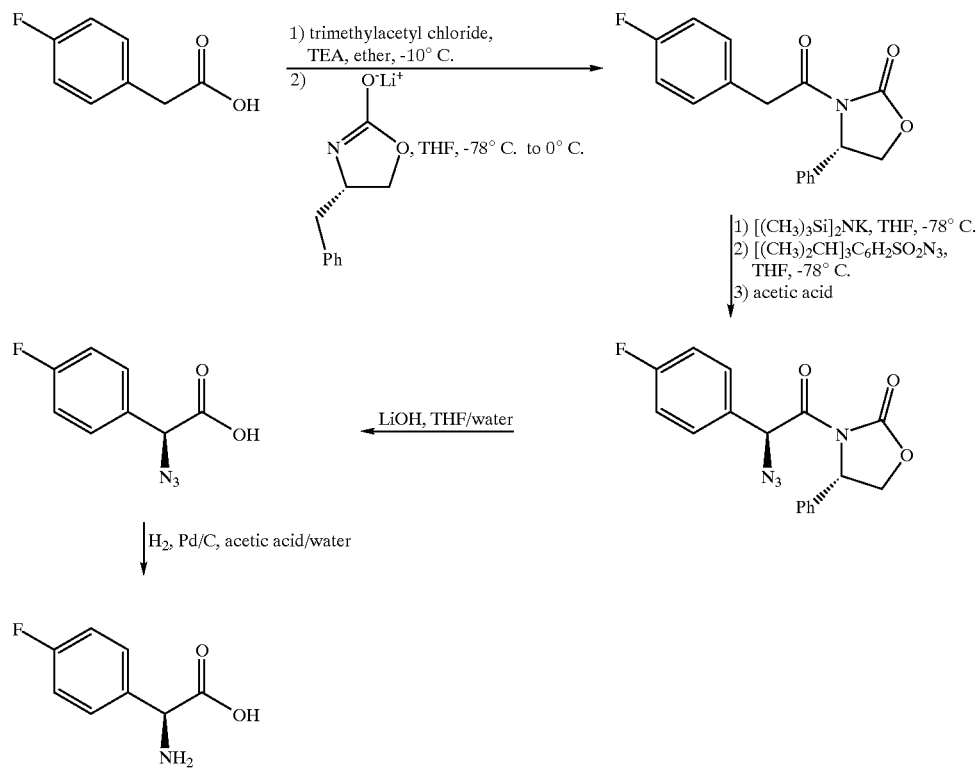

which is based upon the procedure for the asymmetric synthesis of α-amino acids described by D. A. Evans et al., *J. Am. Chem. Soc.*, (1990) 112, 4011-4030.

The complexity of this four-step process combined with the sensitive nature of the protection and double alkylation reactions to give the desired 1,4-oxazin-2-one, renders these prior art syntheses impracticable when attempted on anything other than a laboratory scale.

More recently, in British Patent Specification No. 2,301,588-A (published 11th December 1996) an alternative procedure for the preparation of optically pure N-benzyl-3-(S)-(4-fluorophenyl)-1,4-oxazin-2-one was described which utilizes racemic N-benzyl-3-(4-fluorophenyl)-1,4-oxazin-2-one as starting material and in a minimum of steps affords product of high enantiomeric purity in high yield.

Resolution of racemic N-benzyl-3-(4-fluorophenyl)-1,4-oxazin-2-one is achieved using (−)-3-bromocamphor-8-sulphonic acid (also referred to as (−)-3-BCS) in the presence of a racemising agent.

Whilst this resolution method avoids the need for optically pure starting materials such as (S)-(4-fluorophenyl) glycine, mentioned above, the conventional preparation of racemic N-benzyl-3-(4-fluorophenyl)-1,4-oxazin-2-one via a Strecker reaction between 4-fluorobenzaldehyde and benzylamine followed by alkylation/cyclisation with a two carbon unit, is not without its problems. Not least, the Strecker reaction involves the use of highly toxic cyanide and therefore requires special handling and processing precautions to minimise the risk of exposure of personnel and the environment to cyanide. On a manufacturing scale, the hazards posed by the use of cyanide can greatly increase production costs. There is therefore a need for a process for the preparation of N-benzyl-3-(4-fluorophenyl)-1,4-oxazin-2-one which avoids the use of cyanide.

Agami et al, *Tetrahedron Lett.*, (1993) 34, 7061 describes the reaction of phenylglyoxal with (R)-N-methylphenylglycinol in refluxing acetonitrile to give (5R)-3,5-diphenyl-4-methyl-1,4-oxazin-2-one. Under the same conditions, however, we have found that the reaction of phenylglyoxal with N-benzylethanolamine gives predominantly (>90%) N-benzyl-2-benzoyloxazolidine. The desired product, N-benzyl-3-phenyl-1,4-oxazin-2-one was formed at a low level (5%).

It will be appreciated that N-benzyl-3-(S)-(4-fluorophenyl)-1,4-oxazin-2-one is an important intermediate for a particularly useful class of therapeutic agents. As such, there is a need for the development of a process which is readily amenable to scale-up and hence capable of practical application to the manufacturing plant.

Another important intermediate for the preparation of the useful class of therapeutic agents is N-((S)-(−)-α-methylbenzyl)-3-(S)-(4-fluorophenyl)-1,4-oxazin-2-one (i.e. where the N-benzyl moiety is replaced by a 1-phenylethyl moiety). The process of the present invention is equally applicable to the preparation of such compounds.

The present invention accordingly provides a safe and convenient process for the preparation of racemic N-substituted-3-aryl-1,4-oxazin-2-one derivatives by reaction of an arylglyoxal (either anhydrous or hydrated) with an N-substituted ethanolamine derivative.

In particular, the present invention provides a safe and convenient process for the preparation of racemic N-benzyl-3-(4-fluorophenyl)-1,4-oxazin-2-one and N-((S)-(−)-α-methylbenzyl)-3-(4-fluorophenyl)-1,4-oxazin -2-one by reaction of 4-fluorophenylglyoxal (either anhydrous or hydrated) with N-benzylethanolamine or N-((S)-(−)-α-methylbenzyl)ethanolamine, respectively. The racemic oxazinone products are obtained in high yield and purity.

Thus, in a first aspect of the present invention, there is provided a process for the preparation of a compound of formula (I):

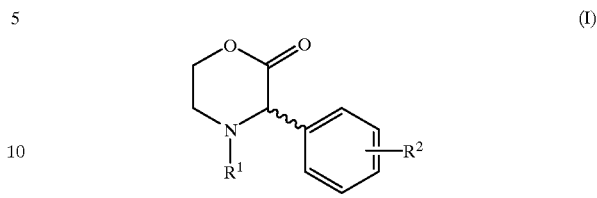

wherein $R^1$ is a $C_{1-6}$alkyl or aryl$C_{1-4}$alkyl group; and $R^2$ is a hydrogen atom, a halogen atom, or a group selected from $C_{1-6}$alkyl, $CF_3$ or $C_{1-6}$alkoxy substituted by $C_{1-4}$alkoxy; which comprises reacting a compound of formula (II) with a compound of formula (III):

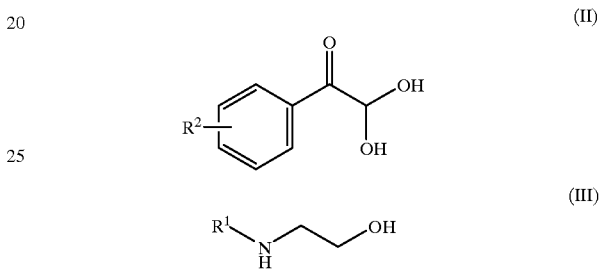

in the presence of an acid. Conveniently, the glyoxal of formula (II) may be either anhydrous or hydrated (as shown).

Suitable acids of use in the reaction include organic acids and inorganic acids. Where an inorganic acid is used, it is preferably anhydrous. Aliphatic and aromatic organic acids are preferred. Examples of suitable acids include aliphatic organic acids such as acetic acid, propanoic acid, butanoic acid and trifluoroacetic acid, aromatic organic acids such as benzoic acid, and anhydrous inorganic acids such as hydrobromic acid and hydrochloric acid. Acetic acid is particularly preferred.

The reaction is conveniently effected in an organic solvent, for example, ethyl acetate, isopropyl acetate or toluene. Isopropyl acetate is particularly preferred.

Particularly preferred compounds of formulae (I) and (III) are those wherein $R^1$ is a benzyl or an α-methylbenzyl group, especially a benzyl or an (S)-(−)-α-methylbenzyl group.

Particularly preferred compounds of formulae (I) and (II) are those wherein $R^2$ is hydrogen, fluorine, chlorine or $CF_3$, preferably hydrogen or fluorine and most especially fluorine. The substituent $R^2$ is preferably attached at the 4-position on the phenyl ring.

According to a further aspect of the present invention, there is provided a process for the preparation of optically pure N-benzyl-3-(S)-(4-fluorophenyl)-1,4-oxazin-2-one which comprises:

(i) contacting racemic N-benzyl-3-(4-fluorophenyl)-1,4-oxazin-2-one with (−)-3-bromocamphor-8-sulphonic acid ((−)-3-BCS) in the presence of a racemising agent;

(ii) collecting the resultant crystalline (−)-3-BCS salt of N-benzyl-3-(S)-(4-fluorophenyl)-1,4-oxazin-2-one; and (iii) liberating the free base of N-benzyl-3-(S)-(4-fluorophenyl)-1,4-oxazin-2-one by the treatment of the (−)-3-BCS salt collected in step (ii) with aqueous base;

characterised in that said racemic N-benzyl-3-(4-fluorophenyl)-1,4-oxazin-2-one is prepared by the reaction between a compound of formula (II) and a compound of formula (III) as described herein.

In this resolution process, the undesired enantiomer remains in solution, where action of the racemising agent results in racemisation to generate more of the desired enantiomer which then crystallises as the (−)-3-BCS salt.

It will be appreciated that following removal of the (−)-3-BCS salt, the crystallisation liquors which contain the undesired enantiomer may be re-worked by the addition, if necessary, of further racemising agent and further (−)-3-BCS thereby increasing the overall yield of the desired enantiomer via the formation of further N-benzyl-3-(S)-(4-fluorophenyl)-1,4-oxazin-2-one (−)-3-BCS salt.

Suitable racemising agents of use in this aspect of the present invention include organic acids such as trifluoroacetic acid or acetic acid, or mineral acids such as hydrochloric acid. Also suitable as a racemising agent is 3-bromocamphor-8-sulphonic acid.

The resolution of racemic N-benzyl-3-(4-fluorophenyl)-1,4-oxazin-2-one with (−)-3-BCS is conveniently effected in a suitable organic solvent, for example, isopropyl acetate or ethyl acetate at a temperature between 0° C. and the boiling point of the solvent, conveniently between room temperature and 100° C., for example, at about 65° C. to 90° C.

Racemisation of the undesired enantiomer may be effected at a temperature between room temperature and the boiling point of the solvent, preferably between 50° C. and 100° C., for example, at about 65° C. to 90° C. Under these conditions resolution continues to take place. The racemisation/resolution is preferably effected over 1 to 9 days, in particular over 1 to 7 days, and preferably over 3 to 6 days.

It will be appreciated that (−)-3-bromocamphor-8-sulphonic acid may conveniently be used to effect both the racemisation and the resolution of racemic N-benzyl-3-(4-fluorophenyl)-1,4-oxazin-2-one. A particularly preferred solvent for use when (−)-3-BCS is used to effect racemisation and resolution is isopropyl acetate.

Where the crystallization liquors are re-worked as described above, additional quantities of the desired chiral oxazinone may be recovered as often as practicable, preferably at least once or twice.

Liberation of the chiral oxazinone free base from the (−)-3-BCS salt is effected using aqueous base, for example, 0.88 ammonia solution or a suitable alkali metal carbonate or hydroxide, such as potassium carbonate, sodium bicarbonate or sodium hydroxide. The free base is conveniently extracted from the (−)-3-BCS using a suitable organic solvent, for example, isopropyl acetate, ethyl acetate or dichloromethane. It will be appreciated that following collection of the liberated free base, the (−)-BCS may also be recovered and recycled using conventional procedures.

When isolating the N-benzyl-3-(S)-(4-fluorophenyl)-1,4-oxazin-2-one (−)-3-BCS salt, it will be appreciated that in order to optimise yield, the reaction mixture should be aged at reduced temperature, for example, at about 0° to 5° C., for at least 1 hour prior to collection of the (−)-3-BCS salt.

The following non-limiting examples illustrate processes according to the present invention. As used herein, diastereomeric excess (d.e.) is measured using the following HPLC system:

Zorbax RX C-8 250×4.6 mm
System A: 0.1% phosphoric acid
System B: acetonitrile
Isocratic 50% A/50% B
1.0 ml/minute
220 nm
Ambient temperature
retention time for S,S isomer=20.5 minutes
retention time for S,R isomer=22.5 minutes As used herein, enantiomeric excess (e.e.) is measured using the following HPLC system:

Chiralcel ODR 250×4.6 mm
43% System A: 0.05M potassium dihydrogen phosphate
57% System B: acetonitrile
0.4 ml/minute
220 nm
45° C.
retention time for S isomer=23.1 minutes
retention time for R isomer=25.7 minutes

EXAMPLE 1

Step (i)

Preparation of 4-Fluorophenylglyoxal Hydrate (Based on the Method Described in *J. Org. Chem.* 1985, 50, 5022–5027)

4-Fluoroacetophenone (27.6 g, 0.2 moles) was dissolved in dimethylsulfoxide (140 ml). 48% Hydrobromic acid (101.1 g, 68.0 ml, 0.6 moles) was added over 20 minutes. The resulting solution was aged at 55–60° C. for 22 hours. The mixture was cooled to room temperature and partitioned between water (1.0 liters) and ethyl acetate (250 ml). The aqueous phase was extracted with ethyl acetate (2×250 ml). The combined ethyl acetate extracts were filtered and solvent switched to toluene at 60° C. under reduced pressure. The solution was diluted to 200 ml with toluene, and water (10 ml) was added. The resulting slurry was stirred at room temperature for 18 hours then at 0° C. for 1 hour. The product was collected by filtration and washed with cold toluene (50 ml). The solid was sucked down on the filter for 30 minutes and air dried to constant weight to afford 4-fluorophenylglyoxal hydrate (24.8 g) as a white solid in 73% yield.

Step (ii)

Through Process to Resolved (S)-N-Benzyl-3-(4-Fluorophenyl)-1,4-Oxazin-2-One.(−)-(3)-Bromocamphor-8-Sulfonic Acid Salt Acetic acid (15 ml) was added to a mixture of 4-fluorophenylglyoxal hydrate (7.4 g, 44 mmoles) and N-benzylethanolamine (6.6 g, 44 moles) in isopropyl acetate (74 ml). The mixture was heated at reflux temperature for 75 minutes then cooled and diluted with isopropyl acetate (200 ml). The mixture was washed with aqueous sodium bicarbonate (250 ml then 50 ml) then water (200 ml). The solution was dried by azeotropic distillation. HPLC Assay showed 12.1 g oxazinone (43 mmoles).

The solution was heated at 60° C. and a solution of (−)-(3)-bromocamphor-8-sulfonic acid in isopropyl acetate (2.17 ml of a 220 g/l solution) added followed by (S)-N-benzyl-3-(4-fluorophenyl-1,4-oxazin-2-one. BCSA salt seed (1.2 g). The slurry was heated at reflux temperature. A solution of (−)-3-bromocamphor-8-sulfonic acid in isopropyl acetate (70.2 ml of a 220 g/l solution) was added over three hours and the slurry heated at reflux temperature for 45 hours then cooled to room temperature. The solid was collected by filtration, washed with isopropyl acetate (20 ml) and dried in vacuum. Yield of (S)-N-benzyl-3-(4-fluorophenyl)-1,4-oxazin-2 one. (−)-3-bromocamphor-8-sulfonic acid salt=22.8 g−1.2 g (seed)=21.6 g (83% yield from 4-fluorophenylglyoxal and N-benzylethanolamine). HPLC profile 99.9 area%, Optical purity 98.8% e.e. by chiral HPLC.

EXAMPLE 2

Preparation of N-((S)-(−)-α-Methylbenzyl)-3-(4-Fluorophenyl)-1,4-Oxazin-2-One

A mixture of 2-(1-(S)-phenylethyl)ethanolamine([CAS 66849-29-4], 5 g, 30 mmol), 4-fluorophenylglyoxal hydrate (5.7 g, 33 mmol) and acetic acid (10 ml) in isopropyl acetate (50 ml) was heated under reflux for 2.5 hours. The mixture was cooled, diluted with isopropyl acetate (100 ml) and washed with water (2×50 ml), aqueous sodium bicarbonate (2×50 ml) then water (25 ml). The solution was filtered then concentrated to low volume by distillation in a vacuum at 50° C. The mixture was flushed with isopropyl acetate (2×100 ml) and the final volume adjusted to 150 ml with isopropyl acetate. The solution was heated to reflux temperature and saturated with HCl gas. After 8 hours the resultant slurry was cooled to room temperature and the product collected by filtration and washed with isopropyl acetate (50 ml). The product was dried in a vacuum at 50° C. to give N-((S)-(−)-α-methylbenzyl)-3-(S)-(4-fluorophenyl)-1,4-oxazin-2-one hydrochloride as a white crystalline solid. (8.76 g) 97.4% d.e. by HPLC, m.p. 202–204° C.

What we claim is:

1. A process for the preparation of a compound of formula (I):

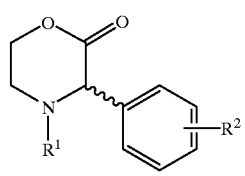

wherein $R^1$ is a $C_{1-6}$alkyl or aryl$C_{1-4}$alkyl group; and $R^2$ is a hydrogen atom, a halogen atom, or a group selected from $C_{1-6}$alkyl, $CF_3$ or $C_{1-6}$alkoxy substituted by $C_{1-4}$alkoxy; which comprises reacting an anhydrous or hydrated glyoxal of formula (II) with a compound of formula (III):

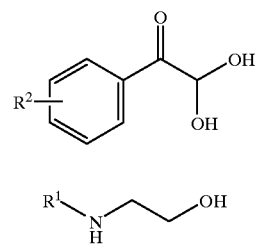

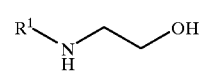

in the presence of an acid.

2. A process as claimed in claim 1 wherein said acid is selected from the group consisting of acetic acid, propanoic acid, butanoic acid, trifluoroacetic acid, benzoic acid, hydrobromic acid and hydrochloric acid.

3. A process as claimed in claim 1 or claim 2 wherein said acid is acetic acid.

4. A process as claimed in claim 1 wherein said process is effected in an organic solvent selected from the group consisting of ethyl acetate, isopropyl acetate and toluene.

5. A process as claimed in claim 4 wherein said organic solvent is isopropyl acetate.

6. A process as claimed in claim 1 wherein $R^1$ is a benzyl or an (α-methylbenzyl) group.

7. A process as claimed in claim 6 wherein $R^1$ is a benzyl or an (S)-(−)-α-methylbenzyl group.

8. A process as claimed in claim 1 wherein $R^2$ is hydrogen, fluorine, chlorine or $CF_3$.

9. A process as claimed in claim 8 wherein $R^2$ is hydrogen or fluorine.

10. A process as claimed in claim 9 wherein $R^2$ is 4-fluorine.

* * * * *